(12) United States Patent
Farrugia et al.

(10) Patent No.: US 9,908,977 B2
(45) Date of Patent: *Mar. 6, 2018

(54) STYRENIC-BASED POLYMER COATED SILVER NANOPARTICLE-SULFONATED POLYESTER COMPOSITE POWDERS AND METHODS OF MAKING THE SAME

(71) Applicant: XEROX CORPORATION, Norwalk, CT (US)

(72) Inventors: Valerie M. Farrugia, Oakville (CA); Barkev Keoshkerian, Thornhill (CA); Michelle N. Chrétien, Mississauga (CA)

(73) Assignee: XEROX CORPORATION, Norwalk, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/098,280

(22) Filed: Apr. 13, 2016

(65) Prior Publication Data
US 2017/0298194 A1  Oct. 19, 2017

(51) Int. Cl.
| | | |
|---|---|---|
| C09D 5/14 | (2006.01) |
| C09D 167/02 | (2006.01) |
| C08J 3/12 | (2006.01) |
| A01N 25/28 | (2006.01) |
| A01N 59/16 | (2006.01) |
| C08G 63/688 | (2006.01) |
| C08J 3/16 | (2006.01) |
| C08J 3/215 | (2006.01) |
| C08K 3/08 | (2006.01) |
| C08L 67/00 | (2006.01) |
| B33Y 10/00 | (2015.01) |
| B33Y 70/00 | (2015.01) |
| B33Y 80/00 | (2015.01) |
| B29C 67/00 | (2017.01) |
| B29C 64/153 | (2017.01) |

(52) U.S. Cl.
CPC .............. *C08J 3/126* (2013.01); *A01N 25/28* (2013.01); *A01N 59/16* (2013.01); *C08G 63/6886* (2013.01); *C08J 3/16* (2013.01); *C08J 3/215* (2013.01); *C08K 3/08* (2013.01); *C08L 67/00* (2013.01); *B29C 64/153* (2017.08); *B29C 67/0077* (2013.01); *B33Y 10/00* (2014.12); *B33Y 70/00* (2014.12); *B33Y 80/00* (2014.12); *C08J 2367/02* (2013.01); *C08J 2425/06* (2013.01); *C08K 2003/0806* (2013.01); *C08K 2201/011* (2013.01)

(58) Field of Classification Search
CPC ............................ B33Y 70/00; B29C 67/0077
See application file for complete search history.

(56) References Cited

U.S. PATENT DOCUMENTS

| | | |
|---|---|---|
| 4,247,508 A | 1/1981 | Housholder |
| 4,863,538 A | 9/1989 | Deckard |
| 5,111,998 A | 5/1992 | Kanda et al. |
| 5,147,753 A | 9/1992 | Hikake |
| 5,272,034 A | 12/1993 | Kawano et al. |
| 5,348,832 A | 9/1994 | Sacripante et al. |
| 5,393,630 A | 2/1995 | Bayley et al. |
| 5,393,807 A | 2/1995 | Farrell |
| 5,597,589 A | 1/1997 | Deckard |
| 5,604,076 A | 2/1997 | Patel et al. |
| 5,648,193 A | 7/1997 | Patel et al. |
| 5,658,704 A | 8/1997 | Patel et al. |
| 5,660,965 A | 8/1997 | Mychajlowskij et al. |
| 5,840,462 A | 11/1998 | Foucher et al. |
| 5,853,944 A | 12/1998 | Foucher et al. |
| 5,916,725 A | 6/1999 | Patel et al. |
| 5,919,595 A | 7/1999 | Mychajlowskij et al. |
| 5,945,245 A | 8/1999 | Mychajlowskij et al. |
| 6,017,671 A | 1/2000 | Sacripante et al. |
| 6,020,101 A | 2/2000 | Sacripante et al. |
| 6,054,240 A | 2/2000 | Julien et al. |
| 6,110,411 A | 8/2000 | Clausen et al. |
| 6,140,003 A | 10/2000 | Sacripante et al. |
| 6,143,457 A | 11/2000 | Carlini et al. |
| 6,210,853 B1 | 4/2001 | Patel et al. |
| 7,312,011 B2 | 12/2007 | Patel et al. |
| 9,243,141 B1 | 1/2016 | Farrugia et al. |
| 2012/0202148 A1 | 8/2012 | Veregin et al. |
| 2015/0290280 A1 | 10/2015 | Petrak et al. |
| 2015/0328835 A1 | 11/2015 | Wu et al. |

FOREIGN PATENT DOCUMENTS

WO    2014075185 A1    5/2015

OTHER PUBLICATIONS

Kundu et al., "Micelle bound redox dye marker for nanogram level arsenic detection promoted by nanoparticles," New J. Chem., 2002, 26, 1081-1084.
Tsavalas, J.G. et al., "Grafting Mechanisms in Hybrid Miniemulsion Polymerization", J. Appl. Polym. Sci., 87:1825-1836 (2003).
Rashid et al., "Synthesis of Silver Nano Particles (Ag-NPs) and their uses for Quantitative Analysis of Vitamin C Tablets", J. Pharm. Sci. 12(1):29-33 (2013).
Ghosh, S.K. et al., "Silver and Gold Nanocluster Catalyzed Reduction of Methylene Bloue by Arsine in a Micellar Medium", Langmuir. 18(23):8756-8760 (2002).
Olson, C.K. et al., "Metabolism of Gluthathione", J. Biol. Chem., 186:731-735 (1950).
Mukherjee et al., "Potential Theranostics Application of Bio-Synthesized Silver Nanoparticies (4-in-1 System)," Theranostics 2014; 4(3)2116-335.

(Continued)

*Primary Examiner* — Gina C Justice
(74) *Attorney, Agent, or Firm* — Pillsbury Winthrop Shaw Pittman LLP (57) ABSTRACT

A composite powder includes a core particle comprising a sulfonated polyester matrix and a plurality of silver nanoparticles dispersed within the matrix, and a shell polymer disposed about the core particle, and methods of making thereof. Various articles can be manufactured from such composite powders.

12 Claims, 5 Drawing Sheets

(56) References Cited

OTHER PUBLICATIONS

Church, J.M. et al ., "Properties of Styrene-Polyester Copolymers" Ind. Eng. Chem., 47 (12):2456-2462 (1955).

FIG. 1A

| GLYCOL MONOMERS | |
|---|---|
| R-GROUP | RELATIVE RATIO |
|  | 35% |
|  | 10% |
|  | 5% |

STYRENIC-BASED POLYMER COATED SILVER NANOPARTICLE-SULFONATED POLYESTER COMPOSITE POWDERS AND METHODS OF MAKING THE SAME

CROSS-REFERENCE TO RELATED APPLICATIONS

Reference is made to commonly owned and co-pending, U.S. patent application Ser. No. 15/098,247 entitled "POLYMER COATED SULFONATED POLYESTER-SILVER NANOPARTICLE COMPOSITE FILAMENTS AND METHODS OF MAKING THE SAME" to Valerie M. Farrugia et al., electronically filed on the same day herewith, the entire disclosures of which are incorporated herein by reference in its entirety.

BACKGROUND

The present disclosure relates to composites, particularly, polymer coated composites comprising metal nanoparticles dispersed throughout the composite matrix, for use in selective laser sintering (SLS) application.

The medical community's reliance on three dimensional 3D printing for various applications is rapidly increasing and covers areas such as tissue and organ fabrication, customizable devices such as prosthetics, mouth guards, orthotics, hearing aids and implants, and pharmaceutical exploration related to controlled drug delivery and personalized drug production. Many of these medical applications require composite material that can inhibit bacterial, microbial, viral or fungal growth. Other products for 3D printing such as kitchen tools, toys, education materials and countless household items also provide a favorable environment for bacteria growth, and therefore antibacterial composite materials are also desirable for use in connection with these products. Due to the layered construction of 3D printed material, the potential for bacterial growth can be very significant, especially since certain bacterial strains can actually thrive within the detailed structural make-up of these materials. Washing alone does not completely sterilize the surfaces and crevasses of these products.

Therefore, there exists a need for new materials with antibacterial properties for 3D printing. One of the 3D printing methods is selective laser sintering (SLS), which is a common additive manufacturing (3D printing) technique. A detailed description of SLS technology can be found in U.S. Pat. Nos. 4,247,508, 4,863,538, 5,017,753, 5,597,589 and 6,110,411, each incorporated herein by reference. SLS printing typically employs powdered plastics/polymers as build materials for printing objects. Most SLS materials are composites of polyamide (nylon) with or without additives such as powdered glass, carbon fibers, aluminum powder, etc. The powder is sintered into shape by a laser in a layer-by-layer fashion to build the objects from "scratch". Laser sintering usually uses particles ranging from about 50 to about 300 microns, where the degree of detail is limited only by the precision of the laser and fineness of the powder. The detail and intricacy of the objects derived through the SLS process is remarkable but also creates potential scaffolds for bacterial or microbial build-up, especially in applications related to health care and the food industry.

SUMMARY

In some aspects, embodiments herein relate to composite powders for use in selective laser sintering (SLS) application, the composite powder comprising a core particle comprising a sulfonated polyester matrix and a plurality of silver nanoparticles dispersed within the matrix; and a shell polymer disposed about the core particle, wherein the silver nanoparticle is present in the composite powder in a range from about 0.5 ppm to about 50,000 ppm; and further wherein the composite powder has a particle size of from about 10 microns to about 300 microns.

In some aspects, embodiments herein relate to method comprising heating a sulfonated polyester resin in an organic-free solvent; adding a solution of silver (I) ion to the heated resin in water to form a mixture; adding a solution of a reducing agent to the mixture, thereby forming an emulsion of particles comprising a sulfonated polyester matrix and a plurality of silver nanoparticles disposed within the sulfonated polyester matrix; adding a styrene monomer and initiator to the emulsion of composite particles to form a shell polymer disposed about the core particles, thereby forming a composite structure; aggregating the emulsion of particles to form aggregated particles; coalescing the aggregated particles to form coalesced particles; and washing the coalesced particles, thereby forming the composite powder.

In some aspects, embodiments herein relate to articles an article comprising a composite powder, the composite powder comprising a core particle and a shell polymer disposed about the core particle, where the core particle comprises a sulfonated polyester matrix and a plurality of silver nanoparticles dispersed within the matrix; wherein the silver nanoparticle is present in the composite powder in a range from about 0.5 ppm to about 50,000 ppm; and further wherein the composite powder has a particle size of from about 10 microns to about 300 microns.

BRIEF DESCRIPTION OF DRAWINGS

Various embodiments of the present disclosure will be described herein below with reference to the figures wherein.

DETAILED DESCRIPTION

As used herein, "a," "an," "the," "at least one," and "one or more" are used interchangeably. Thus, for example, a coating composition that comprises "an" additive can be interpreted to mean that the coating composition includes "one or more" additives.

Also herein, the recitations of numerical ranges includes disclosure of all subranges included within the broader range (e.g., 1 to 5 discloses 1 to 4, 1 to 3, 1 to 2, 2 to 4, 2 to 3, . . . etc.).

The present disclosure provides a composite powder, more specifically, a polymer coated powdered sulfonated polyester polymeric composite containing silver nanoparticles (AgNPs), for use in selective laser sintering (SLS) application.

The class of AgNP polymer composites is more suitable for antibacterial applications compared to ionic and bulk silver, because silver salts may release silver too quickly and uncontrollably while bulk silver is very inefficient in releasing active silver species. AgNPs are known for their antibacterial properties; however the exact mechanism of antibacterial activity using AgNPs is poorly understood. The AgNPs may interact with the cell wall of the bacteria, consequently destabilizing the plasma-membrane potential and reducing the levels of intracellular adenosine triphosphate (ATP) resulting in bacterial cell death. Alternatively, AgNPs might play a role in the formation of reactive oxygen species (ROS) which is responsible for the cytotoxicity of bacteria cells in presence of AgNPs. "Potential Theranostics Application of Bio-Synthesized Silver Nanoparticles (4-in-1 System)," Theranostics 2014; 4(3):316-335. Furthermore, AgNPs have been reported to take part in chemical reduction-oxidation reactions as a catalyst by facilitating electron transfer between an electron donor and electron acceptor. "Micelle bound redox dye marker for nanogram level arsenic detection promoted by nanoparticles," New J. Chem., 2002, 26, 1081-1084.

The SLS composite powder of the present disclosure may be synthesized from sulfonated polyester-silver nanoparticles (SPE-AgNPs). The SLS powder may be formed from the aggregation of self-dispersible sulfonated polyester (SPE) with embedded silver nanoparticles (AgNPs) that are simultaneously formed from silver nitrate with or without a reducing agent during the self-assembly of the sulfonated polyester resin particles in water.

SPE-AgNPs

Figure 1A:
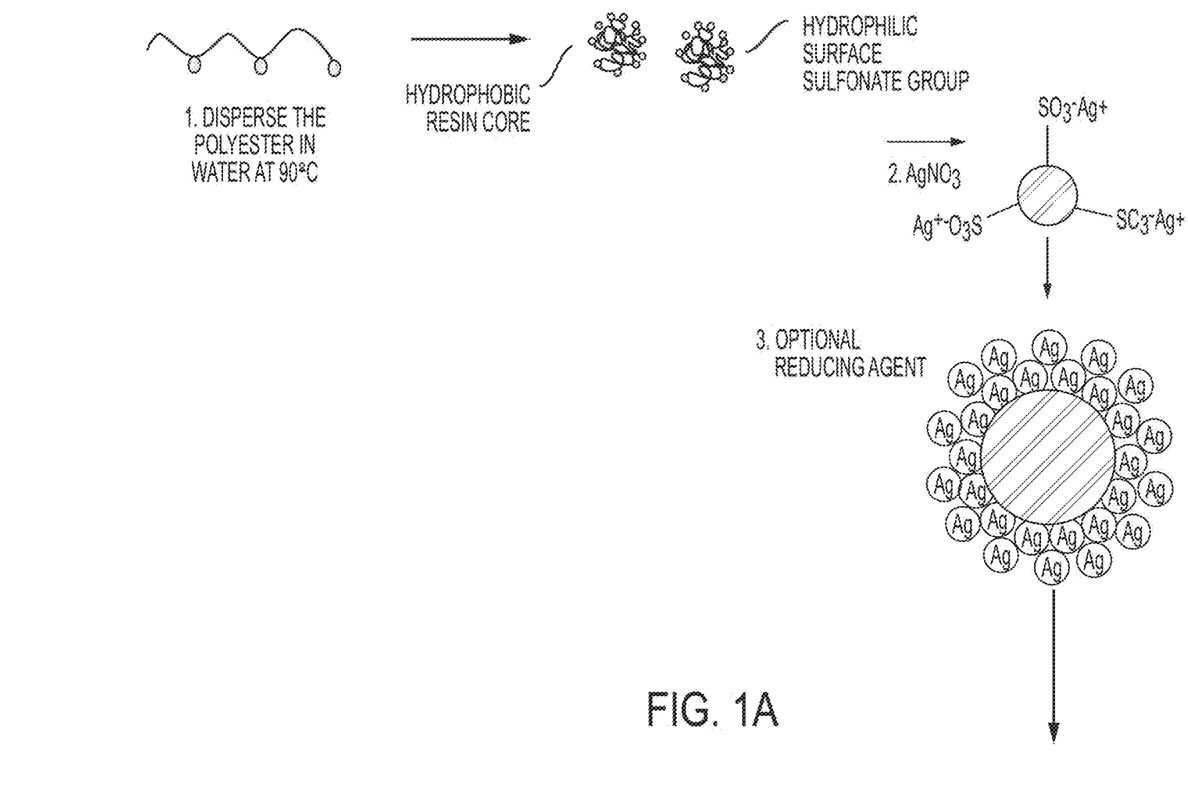
FIGS. 1A and 1B show a schematic of a possible mechanism of styrenation of sulfonated polyester silver nanoparticles (AgNP) in an aqueous medium according to embodiments described herein.
Figure 1B:
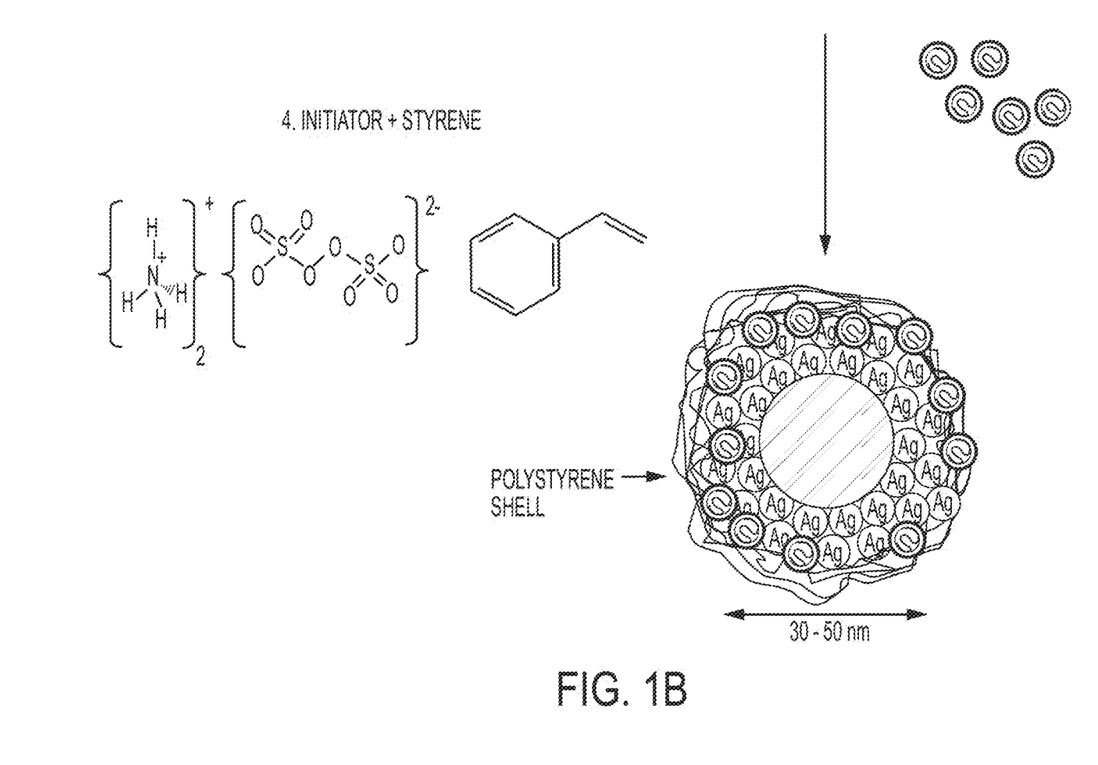

Certain embodiments herein provide methods of synthesizing silver nanoparticles (AgNPs) by reduction of silver (I) ion simultaneously during the self-assembly of sodio sulfonated polyester resin particles in water. The methods which employ water as the bulk solvent are environmentally friendly being free of organic solvents. The methods are efficient requiring minimal time to prepare the polymer metal nanocomposites. Without being bound by theory it is postulated that silver ions are trapped within the polymer matrix during the self-assembly of the sodio sulfonated polyester while simultaneously being reduced to AgNPs. The sulfonated polyester-silver nanoparticles (SPE-AgNPs) are simultaneously synthesized during the self-assembly or dispersing of polymer in water as indicated in FIG. 1. Thus, the sodio sulfonated polyester serves as both a carrier for the silver ions and an organic matrix for the in situ synthesis of silver nanocomposites. An optional reducing agent is added during the self-assembly of sodio sulfonated polyester to reduce silver nitrate into silver nanoparticles (AgNPs) resulting in well dispersed particles. The polyester matrix plays an important role as it is postulated to inhibit the agglomeration of AgNPs. Meanwhile, the porosity of the sulfonated polyester allows the silver ions to diffuse and/or absorb throughout the polymer matrix allowing unhindered interaction with the sulfonate functional groups of the polyester. The reducing agent employed in the reduction of silver ion also freely diffuses throughout the polyester matrix and promotes the formation of well-dispersed AgNPs on the surface and interior of the polyester particles. Advantageously, the process minimizes nanoparticle agglomeration that plagues conventional methods with pre-formed nanoparticles. The sulfonated polymer matrix has an important role in keeping the AgNPs dispersed as well as maintaining overall chemical and mechanical stability of the composite. A polystyrene shell may be then formed on the surface of the SPE-AgNPs. When a hydrophobic monomer, such as styrene is added, it polymerizes around the hydrophobic SPE core of the SPE nanosphere and forms a polystyrene shell on the surface of the SPE-AgNPs. The styrene monomer may diffuse within the porous SPE core. The sulfonated polyester plays a critical role as a stabilizer for in-situ synthesized AgNPs and also as a nano-template to provide a favorable environment for the polymerization of styrene in water without the use of a surfactant.

Silver has many useful properties, including its antibacterial, antimicrobial, antifungal, antiviral properties. These novel properties of the silver nanocomposite materials disclosed herein make them useful in medical applications and others as described herein.

The sulfonated polyester resins disclosed herein have been selected to have a hydrophobic backbone while presenting hydrophilic sulfonate groups attached along the chain. Without being bound by theory, when placed in water and heated, the hydrophobic portions may interact with each other to form a hydrophobic core with the hydrophilic sulfonate groups facing the surrounding water resulting in the sulfonated polyester self-assembling into a higher order, spherical nanoparticle without the requirement of additional reagents. Thus, there is a higher order involving the amphiphilic polyester, in which the hydrophobic backbone, which is insoluble in water, and the water-soluble hydrophilic sulfonate groups, operate as macrosurfactants. This results in self-association, self-assembly, self-dispersible nanoparticles in aqueous medium to yield micelle-like aggregates. The formation of silver nanoparticles within and surrounding the micelles is a secondary occurrence upon addition of silver nitrate and reducing agent.

In embodiments, there are provided composites comprising a sulfonated polyester matrix, and a plurality of silver nanoparticles dispersed within the matrix.

In embodiments, the sulfonated polyester matrix is a branched polymer (BSPE). In embodiments, the sulfonated polyester matrix is a linear polymer. The selection of branched or linear polymer may depend on, inter alia, the downstream application of the composite product. Linear polymers can be used to create strands of fibers or form a strong mesh-like structure. Branched polymers may be useful to confer thermoplastic properties on the resultant composite material.

In embodiments, sulfonated polyesters of the present disclosure can be a homopolymer of one ester monomer or a copolymer of two or more ester monomers. Examples of suitable sulfonated polyesters include those disclosed in U.S. Pat. Nos. 5,348,832, 5,593,807, 5,604,076, 5,648,193, 5,658,704, 5,660,965, 5,840,462, 5,853,944, 5,916,725, 5,919,595, 5,945,245, 6,054,240, 6,017,671, 6,020,101, 6,140,003, 6,210,853 and 6,143,457, the disclosures of each of which are totally incorporated herein by reference.

In embodiments, sulfonated polyesters of the present disclosure can be hydrogen or a salt of a random sulfonated polyester, including salts (such as metal salts, including aluminum salts, salts of alkali metals such as sodium, lithium, and potassium, salts of alkaline earth metals such as beryllium, magnesium, calcium, and barium, metal salts of transition metals, such as vanadium, iron, cobalt, copper, and the like, as well as mixtures thereof) of poly(1,2-propylene-5-sulfoisophthalate), poly(neopentylene-5-sulfoisophthalate), poly(diethylene-5-sulfoisophthalate), copoly(1,2-propylene-5-sulfoisophthalate)-copoly-(1,2-propylene-terephthalate phthalate), copoly(1,2-propylene-diethylene-5-sulfoisophthalate)-copoly-(1,2-propylene-diethylene-terephthalate phthalate), copoly(ethylene-neopentylene-5-sulfoisophthalate)-copoly-(ethylene-neopentylene-terephthalate-phthalate), copoly(propoxylated bisphenol A)-copoly-(propoxylated bisphenol A-5-sulfoisophthalate), copoly(ethylene-terephthalate)-copoly-(ethylene-5-sulfo-isophthalate), copoly(propylene-terephthalate)-copoly-(propylene-5-sulfo-isophthalate), copoly(diethylene-terephthalate)-copoly-(diethylene-5-sulfo-isophthalate), copoly(propylene-diethylene-terephthalate)-copoly-(propylene-diethylene-5-sulfoisophthalate), copoly(propylene-butylene-terephthalate)-copoly(propylene-butylene-5-sulfo-isophthalate), copoly(propoxylated bisphenol-A-fumarate)-copoly(propoxylated bisphenol A-5-sulfo-isophthalate), copoly(ethoxylated bisphenol-A-fumarate)-copoly(ethoxylated bisphenol-A-5-sulfo-isophthalate), copoly(ethoxylated bisphenol-A-maleate)-copoly(ethoxylated bisphenol-A-5-sulfo-isophthalate), copoly(propylene-diethylene terephthalate)-copoly(propylene-5-sulfoisophthalate), copoly(neopentyl-terephthalate)-copoly-(neopentyl-5-sulfoisophthalate), and the like, as well as mixtures thereof.

In general, the sulfonated polyesters may have the following general structure, or random copolymers thereof in which the n and p segments are separated.

wherein R is an alkylene of, for example, from 2 to about 25 carbon atoms such as ethylene, propylene, butylene, oxyalkylene diethyleneoxide, and the like; R' is an arylene of, for example, from about 6 to about 36 carbon atoms, such as a benzylene, bisphenylene, bis(alkyloxy) bisphenolene, and the like; and p and n represent the number of randomly repeating segments, such as for example from about 10 to about 100,000.

Examples of the sulfonated polyesters further include those disclosed in U.S. Pat. No. 7,312,011 which is incorporated herein by reference in its entirety. Specific examples of amorphous alkali sulfonated polyester based resins include, but are not limited to, copoly(ethylene-terephthalate)-copoly-(ethylene-5-sulfo-isophthalate), copoly(propylene-terephthalate)-copoly(propylene-5-sulfo-isophthalate), copoly(diethylene-terephthalate)-copoly(diethylene-5-sulfo-isophthalate), copoly(propylene-diethylene-terephthalate)-copoly(propylene-diethylene-5-sulfo-isophthalate), copoly(propylene-butylene-terephthalate)-copoly(propylene-butylene-5-sulfo-isophthalate), copoly(propoxylated bisphenol-A-fumarate)-copoly(propoxylated bisphenol A-5-sulfo-isophthalate), copoly(ethoxylated bisphenol-A-fumarate)-copoly(ethoxylated bisphenol-A-5-sulfo-isophthalate), and copoly(ethoxylated bisphenol-A-maleate)-copoly(ethoxylated bisphenol-A-5-sulfo-isophthalate), and wherein the alkali metal is, for example, a sodium, lithium or potassium ion. Examples of crystalline alkali sulfonated polyester based resins alkali copoly(5-sulfoisophthaloyl)-co-poly(ethylene-adipate), alkali copoly(5-sulfoisophthaloyl)-copoly(propylene-adipate), alkali copoly(5-sulfoisophthaloyl)-copoly(butylene-adipate), alkali copoly(5-sulfo-isophthaloyl)-copoly(pentylene-adipate), and alkali copoly(5-sulfo-iosphthalbyl)-copoly(octylene-adipate), alkali copoly(5-sulfo-isophthaloyl)-copoly(ethylene-adipate), alkali copoly(5-sulfo-isophthaloyl)-copoly (propylene-adipate), alkali copoly(5-sulfo-isophthaloyl)-co-poly(butylene-adipate), alkali copoly(5-sulfo-isophthaloyl)-copoly(pentylene-adipate), alkali copoly(5-sulfo-isophthaloyl)-copoly(hexylene-adipate), alkali copoly(5-sulfo-isophthaloyl)-copoly(octylene-adipate), alkali copoly(5-sulfoisophthaloyl)-copoly(ethylene-succinate), alkali copoly(5-sulfoisophthaloyl-copoly(butylene-succinate), alkali copoly(5-sulfoisophthaloyl)-copoly(hexylene-succinate), alkali copoly(5-sulfoisophthaloyl)-copoly(octylene-succinate), alkali copoly(5-sulfo-isophthaloyl)-copoly(ethylene-sebacate), alkali copoly(5-sulfo-isophthaloyl)-copoly(propylene-sebacate), alkali copoly(5-sulfo-isophthaloyl)-copoly(butylene-sebacate), alkali copoly(5-sulfo-isophthaloyl)-copoly(pentylene-sebacate), alkali copoly(5-sulfo-isophthaloyl)-copoly(hexylene-sebacate), alkali copoly(5-sulfo-isophthaloyl)-copoly(octylene-sebacate), alkali copoly(5-sulfo-isophthaloyl)-copoly(ethylene-adipate), alkali copoly(5-sulfo-isophthaloyl)-copoly(propylene-adipate), alkali copoly(5-sulfo-iosphthaloyl)-copoly(butylene-adipate), alkali copoly(5-sulfo-isophthaloyl)-copoly(pentylene-adipate), alkali copoly(5-sulfo-isophthaloyl)copoly(hexylene-adipate), poly(octylene-adipate), and wherein the alkali is a metal like sodium, lithium or potassium. In embodiments, the alkali metal is lithium.

The sulfonated polyesters suitable for use in the present disclosure may have a glass transition (Tg) temperature of from about 45° C. to about 95° C., or from about 52° C. to about 70° C., as measured by the Differential Scanning calorimeter. The sulfonated polyesters may have a number average molecular weight of from about 2,000 g per mole to about 150,000 g per mole, from about 3,000 g per mole to about 50,000 g per mole, or from about 6,000 g per mole to about 15,000 g per mole, as measured by the Gel Permeation Chromatograph. The sulfonated polyesters may have a weight average molecular weight of from about 3,000 g per mole to about 300,000 g per mole, from about 8,000 g per mole to about 90,000 g per mole, or from about 10,000 g per mole to about 60,000 g per mole, as measured by the Gel Permeation Chromatograph. The sulfonated polyesters may have a polydispersity of from about 1.6 to about 100, from about 2.0 to about 50, or from about 5.0 to about 30, as calculated by the ratio of the weight average to number average molecular weight.

The linear amorphous polyester resins are generally prepared by the polycondensation of an organic diol and a diacid or diester, at least one of which is sulfonated or a sulfonated difunctional monomer being included in the reaction, and a polycondensation catalyst. For the branched amorphous sulfonated polyester resin, the same materials may be used, with the further inclusion of a branching agent such as a multivalent polyacid or polyol.

Examples of diacid or diesters selected for the preparation of amorphous polyesters include dicarboxylic acids or diesters selected from the group consisting of terephthalic acid, phthalic acid, isophthalic acid, fumaric acid, maleic acid, itaconic acid, succinic acid, succinic anhydride, dodecylsuccinic acid, dodecylsuccinic anhydride, glutaric acid, glutaric anhydride, adipic acid, pimelic acid, suberic acid, azelic acid, dodecanediacid, dimethyl terephthalate, diethyl terephthalate, dimethylisophthalate, diethylisophthalate, dimethylphthalate, phthalic anhydride, diethylphthalate, dimethylsuccinate, dimethylfumarate, dimethylmaleate, dimethylglutarate, dimethyladipate, dimethyl dodecylsuccinate, and mixtures thereof. The organic diacid or diester are selected, for example, from about 45 to about 52 mole percent of the resin. Examples of diols utilized in generating the amorphous polyester include 1,2-propanediol, 1,3-propanediol, 1,2-butanediol, 1,3-butanediol, 1,4-butanediol, pentanediol, hexanediol, 2,2-dimethylpropanediol, 2,2,3-trimethylhexanediol, heptanediol, dodecanediol, bis(hyroxyethyl)-bisphenol A, bis(2-hyroxypropyl)-bisphenol A, 1,4-cyclohexanedimethanol, 1,3-cyclohexanedimethanol, xylenedimethanol, cyclohexanediol, diethylene glycol, bis (2-hydroxyethyl) oxide, dipropylene glycol, dibutylene, and mixtures thereof. The amount of organic diol selected can vary, and more specifically, is, for example, from about 45 to about 52 mole percent of the resin.

Alkali sulfonated difunctional monomer examples, wherein the alkali is lithium, sodium, or potassium, include dimethyl-5-sulfo-isophthalate, dialkyl-5-sulfo-isophthalate-4-sulfo-1,8-naphthalic anhydride, 4-sulfo-phthalic acid, 4-sulfophenyl-3,5-dicarbomethoxybenzene, 6-sulfo-2-naphthyl-3,5-dicarbomethoxybenzene, sulfo-terephthalic acid, dimethyl-sulfo-terephthalate, dialkyl-sulfo-terephthalate, sulfo-ethanediol, 2-sulfo-propanediol, 2-sulfo-butanediol, 3-sulfo-pentanediol, 2-sulfo-hexanediol, 3-sulfo-2-methyl-pentanediol, N,N-bis(2-hydroxyethyl)-2-aminoethane sulfonate, 2-sulfo-3,3-dimethylpent-anediol, sulfo-p-hydroxybenzoic acid, mixtures thereto, and the like. Effective difunctional monomer amounts of, for example, from about 0.1 to about 2 weight percent of the resin can be selected.

Branching agents for use in forming the branched amorphous sulfonated polyester include, for example, a multivalent polyacid such as 1,2,4-benzene-tricarboxylic acid, 1,2,4-cyclohexanetricarboxylic acid, 2,5,7-naphthalenetricarboxylic acid, 1,2,4-naphthalenetricarboxylic acid, 1,2,5-hexanetricarboxylic acid, 1,3-dicarboxyl-2-methyl-2-methylene-carboxylpropane, tetra(methylene-carboxyl)methane, and 1,2,7,8-octanetetracarboxylic acid, acid anhydrides thereof, and lower alkyl esters thereof, 1 to about 6 carbon atoms; a multivalent polyol such as sorbitol, 1,2,3,6-hexanetetrol, 1,4-sorbitane, pentaerythritol, dipentaerythritol, tripentaerythritol, sucrose, 1,2,4-butanetriol, 1,2,5-pentatriol, glycerol, 2-methylpropanetriol, 2-methyl-1,2,4-butanetriol, trimethylolethane, trimethylolpropane, 1,3,5-trihydroxymethylbenzene, mixtures thereof, and the like. The branching agent amount selected is, for example, from about 0.1 to about 5 mole percent of the resin.

Polycondensation catalyst examples for amorphous polyesters include tetraalkyl titanates, dialkyltin oxide such as dibutyltin oxide, tetraalkyltin such as dibutyltin dilaurate, dialkyltin oxide hydroxide such as butyltin oxide hydroxide, aluminum alkoxides, alkyl zinc, dialkyl zinc, zinc oxide, stannous oxide, or mixtures thereof; and which catalysts are selected in amounts of, for example, from about 0.01 mole percent to about 5 mole percent based on the starting diacid or diester used to generate the polyester resin.

In particular embodiments, the sulfonated polyester matrix comprises a polyol monomer unit selected from the group consisting of trimethylolpropane, 1,2-propanediol, diethylene glycol, and combinations thereof.

In particular embodiments, the sulfonated polyester matrix comprises a diacid monomer unit selected from the group consisting of terephthalic acid, sulfonated isophthalic acid, and combinations thereof.

In embodiments, the sulfonated polyester-silver core nanoparticles may have a particle size in a range from about 5 nm to about 500 nm, or about 10 to about 200 nm, or about 20 to about 100 nm. A core particle size of less than 100 nm may be useful for reinforcement of polymer matrices without disturbing transparency and other properties of coatings.

Tsavalas, J. G. et al. J. Appl. Polym. Sci., 87:1825-1836 (2003). As used herein, references to "particle size" will generally refer to $D_{50}$ mass-median-diameter (MMD) or the log-normal distribution mass median diameter. The MMD is considered to be the average particle diameter by mass.

In embodiments, the silver nanoparticles may include solely elemental silver or may be a silver composite, including composites with other metals. Such metal-silver composite may include either or both of (i) one or more other metals and (ii) one or more non-metals. Suitable other metals include for example Al, Au, Pt, Pd, Cu, Co, Cr, In, and Ni, particularly the transition metals for example Au, Pt, Pd, Cu, Cr, Ni, and mixtures thereof. Exemplary metal composites are Au—Ag, Ag—Cu, Au—Ag—Cu, and Au—Ag—Pd. Suitable non-metals in the metal composite include for example Si, C, and Ge. The various components of the silver composite may be present in an amount ranging for example from about 0.01% to about 99.9% by weight, particularly from about 10% to about 90% by weight. In embodiments, the silver composite is a metal alloy composed of silver and one, two or more other metals, with silver comprising for example at least about 20% of the nanoparticles by weight, particularly greater than about 50% of the nanoparticles by weight. Unless otherwise noted, the weight percentages recited herein for the components of the silver-containing nanoparticles do not include the stabilizer.

Silver nanoparticles composed of a silver composite can be made for example by using a mixture of (i) a silver compound (or compounds, especially silver (I) ion-containing compounds) and (ii) another metal salt (or salts) or another non-metal (or non-metals) during the reduction step.

In embodiments, the silver nanoparticles have a particle size in a range from about 2 to about 50 nm, or about 10 to about 50 nm or about 20 to about 50 nm. Silver nanoparticles of diameter less than 100 nm absorb light primarily below 500 nm. This property is useful as it allows the AgNPs to be used in combination with fluorescence emission detection since most fluorophores emit at a wavelength above 500 nm, thus minimizing quenching of the signal.

In embodiments, the sulfonated polyester-silver core nanoparticles may further comprise nanostructured materials, such as, without limitation, carbon nanotubes (CNTs, including single-walled, double-walled, and multi-walled), graphene sheet, nanoribbons, nano-onions, hollow nanoshell metals, nano-wires and the like. In embodiments, CNTs may be added in amounts that enhance electrical and thermal conductivity.

A shell polymer may be disposed over the sulfonated polyester-silver core nanoparticles to provide additional reinforcement in terms of the hardness, strength, chemical resistance and thermal stability of the sulfonated polyester-silver core/AgNP composite in extreme environments.

In embodiments, the shell polymer disposed about the sulfonated polyester-silver core nanoparticles comprises a styrene monomer, including substituted or unsubstituted styrenes. In embodiments, the shell polymer further comprises at least one vinyl monomer selected from the group consisting of methyl acrylate, ethyl acrylate, butyl acrylate, isobutyl acrylate, dodecyl acrylate, n-octyl acrylate, 2-ethylhexyl acrylate, 2-chloroethyl acrylate, phenyl acrylate, β-carboxyethyl acrylate, methyl α-chloro acrylate, methyl methacrylate, ethyl methacrylate, butyl methacrylate, butadiene, isoprene, methacrylonitrile, acrylonitrile, methyl vinyl ether, vinyl isobutyl ether, vinyl ethyl ether, vinyl acetate, vinyl propionate, vinyl benzoate, vinyl butyrate, vinyl methyl ketone, vinyl hexyl ketone, and methyl isopropenyl ketone, vinylidene chloride, vinylidene chloro fluoride, N-vinylindole, N-vinyl pyrrolidene, acrylic acid, methacrylic acid, acrylamide, methacrylamide, vinyl pyridine, vinyl pyrrolidone, vinyl N-methylpyridinium chloride, vinyl naphthalene, p-chlorostyrene, vinyl chloride, vinyl fluoride, ethylene, propylene, butylene, and isobutylene.

In embodiments, the shell polymer has a thickness from about 0.5 nm to about 100 nm, or from about 1.0 nm to about 50 nm, or from about 1.5 nm to about 20 nm.

In embodiments, the shell polymer confers to the sulfonated polyester-silver core nanoparticles one or more properties, such as, methanol resistance, resistance to thermal degradation, and acid/base resistance.

With respect to methanol resistance, it is postulated that the polymer shell protects the core sulfonated polyester/AgNP composite from gelation. In embodiments, no more than about 10% material dissolves when, for example, a styrene shell is used.

With respect to resistance to thermal degradation, polymer shell-protected composites show only about 50% degradation at 400° C., while uncoated SPE-AgNP composites show about 80% decomposition at 400° C. The thermal stability of the styrene-coated composites, in particular, appears to be more complex than that of polystyrene alone.

With respect to acid/base resistance, addition of a polymer shell, such as styrene, to the core composite may provide an improvement under basic conditions by 20 to 30%. Finally, a polymer shell, such as polystyrene, around the SPE/AgNp core provides substantially improved rigidity and strength of the organic/inorganic hybrid composite core materials.

Composite powder synthesized from polymeric coated sulfonated polyester-silver nanoparticles SPE-AgNPs Composite powders disclosed herein are specifically suitable for SLS printing, which can be prepared from the sulfonated polyester-silver nanoparticles (SPE-AgNPs).

Composite powders of the present disclosure may be prepared by conventional (ground and classification) or chemical (emulsion aggregation) means. U.S. Pat. Nos. 5,111,998, 5,147,753, 5,272,034, and 5,393,630 disclose conventional toner manufacturing processes are incorporated in their entirety by reference herein.

Figure 3:
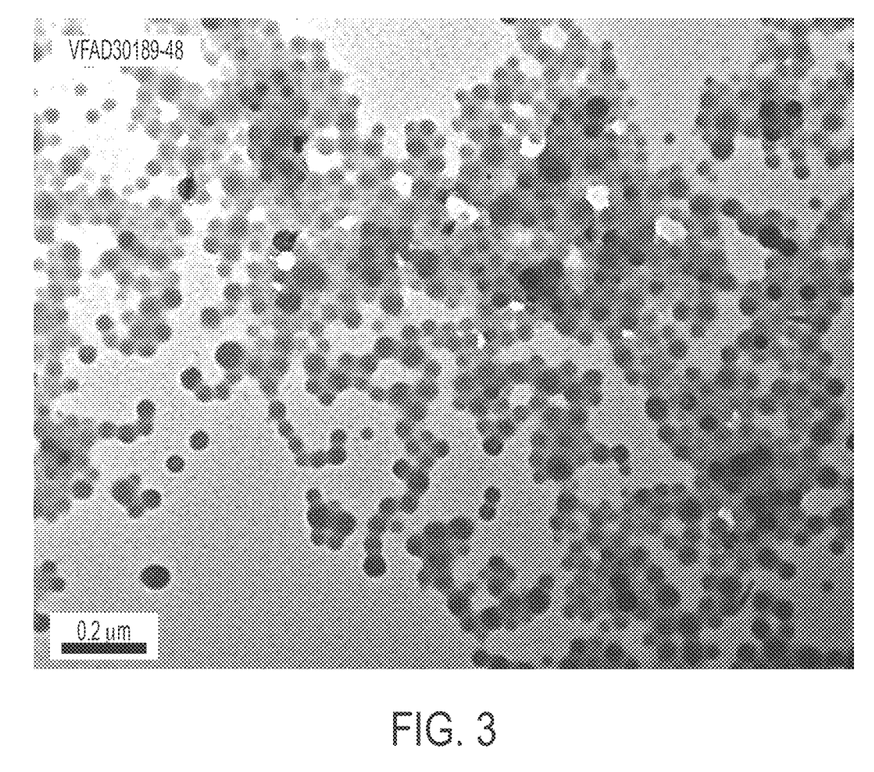
FIG. 3 shows a Transmission Electron Microscopy (TEM) image of an exemplary composite structure (Example 4) comprising a styrene-coated, sulfonated polyester-AgNP composite structure. Dark areas are AgNPs.

Composite powders may be prepared by emulsion aggregation means. Any suitable emulsion aggregation procedure may be used in forming the emulsion aggregation composite particles without restriction. FIG. 3 shows an emulsion aggregation process for preparing dry particles for selective laser sintering (SLS) according to certain embodiments of the present disclosure. These procedures typically include the process steps of aggregating an emulsion of particles, such as those described in the present disclosure, a polymer coated core particle, where the core particle comprising a sulfonated polyester matrix and a plurality of silver nanoparticles disposed within the sulfonated polyester matrix, and one or more additional optional additives to form aggregated particles, subsequently coalescing the aggregated particles, and then recovering, optionally washing and optionally drying the obtained emulsion aggregation particles. However, in embodiments, the process is modified by the addition of a coalescent agent (or coalescence aid agent) prior to the coalescence. This addition of the coalescent agent provides toner particles having improved spheroidization, and allows the coalescence to be conducted in a shorter time, at a lower process temperature, or both. In embodiments, prior to the aggregation step, water is added to the SPE-AgNPs to form a slurry. In embodiments, the addition of water affords a total solid content based on the total weight of the slurry of from about 1% to about 40%, from about 5% to about 20%, or from about 10% to about 50%.

The aggregating step includes heating the slurry to a temperature of from about 30° C. to about 80° C., from about 40° C. to about 70° C., or from about 50° C. to about 68° C. The duration of the aggregation step may be from about 1 minute to about 8 hours, from about 30 minutes to about 6 hour, or from about 60 minutes to about 4 hours. The coalescing step includes heating the aggregated particles to a temperature of from about 30° C. to about 95° C., from about 40° C. to about 95° C., or from about 60° C. to about 90° C. The duration of the coalescing step may be from about 1 minute to about 6 hours, from about 30 minutes to about 4 hour, or from about 60 minutes to about 3 hours.

Examples of suitable coalescent agents include, but are not limited to, benzoic acid alkyl esters, ester-alcohols, glycol-ether type solvents, long-chain aliphatic alcohols, aromatic alcohols, mixtures thereof, and the like. Examples of benzoic acid alkyl esters include benzoic acid alkyl esters where the alkyl group, which can be straight or branched, substituted or unsubstituted, has from about 2 to about 30 carbon atoms, such as decyl or isodecyl benzoate, nonyl or isononyl benzoate, octyl or isooctyl benzoate, 2-ethylhexyl benzoate, tridecyl or isotridecyl benzoate, 3,7-dimethyloctyl benzoate, 3,5,5-trimethylhexyl benzoate, mixtures thereof, and the like. Specific commercial examples of such benzoic acid alkyl esters include VELTA® 262 (isodecyl benzoate) and VELTA® 368 (2-ethylhexyl benzoate), available from Vlesicol Chemical Corporation. Examples of ester-alcohols include hydroxyalkyl esters of alkanoic acids where the alkyls group, which can be straight or branched, substituted or unsubstituted, independently have from about 2 to about 30 carbon atoms, such as 2,2,4-trimethylpentane-1,3-diol monoisobutyrate. Specific commercial examples of such ester-alcohols include TEXANOL® (2,2,4-trimethylpentane-1,3-diol monoisobutyrate) available from Eastman Chemical Company. Examples of glycol-ether type solvents include diethylene glycol monomethylether acetate, diethylene glycol monobutylether acetate, butyl carbitol acetate (BCA), and the like. Examples of long-chain aliphatic alcohols include those where the alkyl group is from about 5 to about 20 carbon atoms, such as ethylhexanol, octanol, dodecanol, and the like. Examples of aromatic alcohols include benzyl alcohol, and the like.

In embodiments, the coalescent agent (or coalescence aid agent) evaporates during later stages of the emulsion aggregation process or during coalescence, such as during the heating step that is generally near or above the glass transition temperature of the sulfonated polyester resin. The final composite powders are thus free of, or essentially or substantially free of, any remaining coalescent agent. To the extent that any remaining coalescent agent may be present in the final powder composites, the amount of remaining coalescent agent is such that it does not affect any properties or performance of the composite powders.

The coalescent agent can be added prior to the coalescence in any desired or suitable amount. For example, the coalescent agent can be added in an amount of from about 0.01 to about 10 percent by weight, based on the solids content in the reaction medium. For example, the coalescent agent can be added in an amount of from about 0.05 or from about 0.1 to about 0.5 or to about 5.0 percent by weight, based on the solids content in the reaction medium. In embodiments, the coalescent agent can be added at any time between aggregation and coalescence (also upfront before heating)

Optional additives such as waxes, pigments, ceramics, carbon fiber or nanotubes, and fillers may be included in the composite powder. These additives may be added prior to or during the aggregation step or upfront before heating. The amount of additives present in the composite powder may be from about 0% to about 30%, from about 0% to about 20%, or from about 0% to about 10% by weight of the total weight of the composite powder.

The final composite powders can be of any desired size, in embodiments, the composite powders may have a particle size of from about 10 microns to about 300 microns, from about 10 microns to about 100 microns, or from about 10 microns to about 50 microns. The use of composite powders in the smaller particle size range (e.g., 5-20 microns) may be advantageous in SLS relative to the typical particle size ranges (100-300 microns) due to the fine-grained nature of the shapes thus available. In embodiments, the composite powders have a particle size distribution with a lower number ratio geometric standard deviation (GSD) of from about 1.0 to about 4.0, from about 1.1 to about 3.0, or from about 1.2 to about 2.0. The toner particles of the present disclosure also can have a size such that the upper geometric standard deviation (GSD) by volume is from about 1.0 to about 4.5, from about 1.1 to about 3.5, or from about 1.2 to about 2.5.

The final composite powders can be of any desired shape, either coarse or spherical. Spherical particles are generally desired for optimal packing and fusing/welding.

In embodiments, a loading of silver nanoparticle is present in the final composite powders is in a range from about 0.5 ppm to about 50,000 ppm, from about 5 ppm to about 5,000, from about 10 ppm to about 2,500, ppm, or from about 50 ppm to about 1,000 ppm. Loading concentrations of silver within this range can be used for antibacterial applications. Lower concentrations of silver might be sufficient for catalytic applications; concentrations of AgNPs as low as 1 ppm have been used. Ghosh, S. K. et al. Langmuir. 18(23):8756-8760 (2002).

In embodiments, there are provided articles comprising a plurality of composite powder as described herein, the composite powder may comprise a core particle comprising a sulfonated polyester matrix and a plurality of silver nanoparticles dispersed throughout the matrix and a shell polymer disposed about the core particle.

The properties of the composite powder herein make them useful in various applications including, without limitation, electronics components, optical detectors, chemical and biochemical sensors and devices. The ability to miniaturize any of these materials is a major benefit of using the nanoscale composite structures herein. Other areas of interest that employ the composite powder herein include, without limitation, antibacterial applications, optical bi-stability, textiles photoresponsivity, environmental, biological, medicine (membranes and separation devices), functional smart coatings, fuel and solar cells, and as catalysts.

Method of Making

The present disclosure also provides methods for making the composite powder described herein. The method to prepare the microparticles from polymeric coated sulfonated polyester-silver nanoparticles SPE-AgNPs is similar to the process known to generate toner particles (emulsion aggregation or EA). Particles of narrow size distribution and controllable particle size can be achieved with the aid of aggregating agents such as zinc acetate, magnesium chloride salts, aluminum sulfate and polyaluminum chloride (PAC). The particle morphology can be controlled via temperature, time, and stirring to provide particles that range from an irregularly shaped or an imperfect spherical to a near or perfect spherical.

The method comprising heating a sulfonated polyester resin in water, adding a solution of silver (I) ion to the heated resin in water to form a mixture, adding a solution of a reducing agent to the mixture, thereby forming an emulsion of composite particles comprising a sulfonated polyester matrix and a plurality of silver nanoparticles disposed within the sulfonated polyester matrix; adding a styrene monomer and initiator to the emulsion of composite particles to form a shell polymer disposed about the core particles, thereby forming a composite structure; aggregating the emulsion of particles to form aggregated particles; coalescing the aggregated particles to form coalesced particles; and washing the coalesced particles, thereby forming the composite powder.

In embodiments, heating is conducted at a temperature from about 65° C. to about 90° C. Temperatures in this range are appropriate for both the initial dissolution of the polymer resin and subsequent reduction in the presence of silver ion.

In embodiments, a source of silver (I) ion is selected from silver nitrate, silver sulfonate, silver fluoride, silver perchlorate, silver lactate, silver tetrafluoroborate, silver oxide, silver acetate. Silver nitrate is a common silver ion precursor for the synthesis of AgNPs.

In embodiments, the reducing agent is selected from ascorbic acid, trisodium citrate, glucose, galactose, maltose, lactose, gallic acid, rosmarinic acid, caffeic acid, tannic acid, dihydrocaffeic acid, quercetin, sodium borohydride, potassium borohydride, hydrazine hydrate, sodium hypophosphite, hydroxylamine hydrochloride. In embodiments, reducing agents for the synthesis of AgNPs may include sodium borohydride or sodium citrate. Selection of appropriate reducing agent may provide access to desirable nanoparticle morphologies. For example, ascorbic acid was observed to provide silver nanoplate forms during a study directed to quantitation of vitamin C tablets. Rashid et al. *J. Pharm. Sci.* 12(1):29-33 (2013).

In embodiments, methods may include during addition of styrene monomer, also adding at least one vinyl monomer selected from the group consisting of methyl acrylate, ethyl acrylate, butyl acrylate, isobutyl acrylate, dodecyl acrylate, n-octyl acrylate, 2-ethylhexyl acrylate, 2-chloroethyl acrylate, phenyl acrylate, 3-carboxyethyl acrylate, methyl α-chloro acrylate, methyl methacrylate, ethyl methacrylate, butyl methacrylate, butadiene, isoprene, methacrylonitrile, acrylonitrile, methyl vinyl ether, vinyl isobutyl ether, vinyl ethyl ether, vinyl acetate, vinyl propionate, vinyl benzoate, vinyl butyrate, vinyl methyl ketone, vinyl hexyl ketone, and methyl isopropenyl ketone, vinylidene chloride, vinylidene chloro fluoride, N-vinylindole, N-vinyl pyrrolidene, acrylic acid, methacrylic acid, acrylamide, methacrylamide, vinyl pyridine, vinyl pyrrolidone, vinyl N-methylpyridinium chloride, vinyl naphthalene, p-chlorostyrene, vinyl chloride, vinyl fluoride, ethylene, propylene, butylene, and isobutylene.

In embodiments, methods disclosed herein may be particularly well-suited for making composites with relatively low solids content. Under such conditions, silver ion and reducing agent may readily diffuse through the polymer matrix. In the case of silver ion, such ready diffusion may improve uniformity of distribution of silver throughout the matrix.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

General Process: Composite preparation involves dispersing a branched sodio sulfonated polyester (BSPE) in water at about 90° C., followed by addition of a silver nitrate solution and lastly a mild reducing agent such as trisodium citrate, ascorbic acid. The reduction of Ag(I) to Ag(0) occurs after the addition of Ag(I) salt to the BSPE and is facilitated by the reducing agent. AgNP-BSPE systems that are synthesized via the trisodium citrate reductant route can also utilize the citrate cap for further applications such as biosensors where the citrate ligand is employed for analyte binding for quantitative or qualitative analysis of analyte concentration in a sample. Lastly, a polymeric monomer, such as a styrene monomer, along with an initiator (e.g., ammonium persulfate) is added to form a polymeric shell about the core particle.

Example 1

This example describes the preparation of a branched sodio sulfonated amorphous polyesters (BSPE) according to embodiments of the present disclosure A branched amorphous sulfonated polyester resin comprised of 0.425 mole equivalent of terephthalate, 0.080 mole equivalent of sodium 5-sulfoisophthalic acid, 0.4501 mole equivalent of 1,2-propanediol, and 0.050 mole equivalent of diethylene glycol, was prepared as follows. In a one-liter Parr reactor equipped with a heated bottom drain valve, high viscosity double turbine agitator, and distillation receiver with a cold water condenser was charged 388 grams of dimethylterephthalate, 104.6 grams of sodium 5-sulfoisophthalic acid, 322.6 grams of 1,2-propanediol (1 mole excess of glycols), 48.98 grams of diethylene glycol, (1 mole excess of glycols), trimethylolpropane (5 grams) and 0.8 grams of butyltin hydroxide oxide as the catalyst. The reactor was heated to 165° C. with stirring for 3 hours and then again heated to 190° C. over a one hour period, after which the pressure was slowly reduced from atmospheric pressure to about 260 Torr over a one hour period, and then reduced to 5 Torr over a two hour period. The pressure was then further reduced to about 1 Torr over a 30 minute period and the polymer was discharged through the bottom drain onto a container cooled with dry ice to yield 460 grams of sulfonated-polyester resin. The branched sulfonated-polyester resin had a glass transition temperature measured to be 54.5° C. (onset) and a softening point of 154° C.

Example 2

This Comparative Example shows the preparation of a BSPE core particle with no silver and no styrene shell The reaction was carried out in a 3 necked, 500 mL round bottom flask equipped with an overhead stirrer, reflux condenser, thermocouple, hot plate, and nitrogen entrance (the condenser acted as the nitrogen exit). 125 mL of deionized water (DIW) was charged into the flask at room temperature (about 22° C.). The DIW was heated to 90° C. with stirring while nitrogen running through the solution (RPM=330). Then 50.0 g of finely ground, solid BSPE obtained from Example 1 was added to the DIW (RPM=400). The solution was stirred at 90° C. for 2 hours (RPM=400). An BSPE emulsion was obtained and cooled to room temperature with stirring (RPM=400). The final appearance of the BSPE emulsion was a white, opaque solution.

Example 3

This Comparative Example shows the formation of a styrene shell about a BSPE core particle with no silver dispersed within the core particle.

The reaction was carried out in a 3 necked, 500 mL round bottom flask equipped with an overhead stirrer, reflux condenser, thermocouple, hot plate, and nitrogen entrance (the condenser acted as the nitrogen exit). About 240 mL of deionized water was charged into the flask at room temperature (22° C.). The heat was turned on and set to 90° C. and nitrogen was run through the system for 30 minutes (RPM=300). Once the temperature had stabilized, 50.0 g of finely ground BSPE obtained from Example 1 was added to the flask (RPM=300). The resulting solution was translucent with a blue tinge, which was left to stir for 2 hours. Then the set point was reduced to 75° C. Once the temperature had stabilized, 3.6 g styrene (9% of total monomer) was added, followed by dropwise addition of an ammonium persulfate solution (0.08 g ammonium persulfate dissolved in 10 mL deionized water) which acts as an initiator. The addition of ammonium persulfate solution causes a slight increase in temperature (exotherm). After the temperature had stabilized at 75° C., 36.40 g styrene monomer was added dropwise over 15 minutes to the mixture. The resulting solution was white and opaque after monomer addition was complete. The reaction was allowed to be stirred for 2 hours at 75° C., and then allowed to cool to room temperature. The final appearance was a white, opaque solution.

Example 4

This Example shows the formation of a styrene shell about a BSPE/AgNP core composite prepared in the absence of a reducing agent.

The reaction was carried out in a 3 necked, 500 mL round bottom flask equipped with an overhead stirrer, reflux condenser, thermocouple, hot plate, and nitrogen entrance (the condenser acted as the nitrogen exit). About 235 mL of deionized water was charged into the flask at room temperature (22° C.). The heat was turned on and set to 90° C. and nitrogen was run through the system for 30 minutes (RPM=300). Once the temperature had stabilized, 50.0 g of finely ground BSPE obtained from Example 1 was added to the flask (RPM=330). The resulting mixture was translucent with a blue tinge, which was left to stir for 2 hours. 0.12 g of $AgNO_3$ was dissolved in 10 mL deionized water and added to the solution dropwise (1 drop/second). A colour change to dark brown with a yellow tinge was observed. After the completion of $AgNO_3$ addition, the set point was reduced to 75° C. Once the temperature had stabilized, 3.6 g styrene (9% of total monomer) was added, followed by dropwise addition of an ammonium persulfate solution (0.08 g ammonium persulfate dissolved in 5 mL deionized water) which acts as an initiator. Ammonium persulfate solution causes a slight increase in temperature (exotherm). After the temperature had stabilized at 75° C., 36.40 g styrene monomer was added dropwise over 40 minutes to the mixture. The resulting solution was light pink and opaque after monomer addition was complete. The reaction was allowed to be stirred for 2 hours at 75° C. and then allowed to cool to room temperature. The final appearance was a light pink, opaque solution.

Example 5

This Example shows the formation of a styrene shell about a BSPE/AgNP core particle prepared in the presence of the reducing agent oleic acid.

The reaction was carried out in a 3 necked, 500 mL round bottom flask equipped with an overhead stirrer, reflux condenser, thermocouple, hot plate, and nitrogen entrance (the condenser acted as the nitrogen exit). About 118 mL of deionized water and 0.25 g oleic acid were charged into the flask at room temperature (22° C.). The heat was turned on and set to 90° C. and nitrogen was run through the system for 30 minutes (RPM=300). Once the temperature had stabilized, 25.0 gram of finely ground BSPE obtained from Example 1 was added to the flask (RPM=250). The resulting solution was translucent and purple/brown in colour. The mixture was left to stir for 2 hours. 0.12 g of $AgNO_3$ was dissolved in 5 mL distilled water and added to the solution dropwise (1 drop/second). A colour change to dark brown was observed. After the completion of $AgNO_3$ addition, the set point was reduced to 75° C. (RPM=330). Once the temperature had stabilized, 20.0 g of styrene was added, followed by dropwise addition of an ammonium persulfate solution (0.05 g ammonium persulfate dissolved in 2 mL deionized water) which acts as an initiator. The reaction was run for 4 hours at 75° C., and then for another 16.5 hours at 60° C. (RPM=330). The resulting solution was then allowed to cool to room temperature. The final appearance was a brown opaque solution.

Example 6

This Example shows the formation of a styrene shell about a BSPE/AgNP core particle prepared in the presence of the reducing agent glutathione.

The reaction was carried out in a 3 necked, 500 mL round bottom flask equipped with an overhead stirrer, reflux condenser, thermocouple, hot plate, and nitrogen entrance (the condenser acted as the nitrogen exit). About 240 mL of deionized water was charged into the flask at room temperature (22° C.). The heat was turned on and set to 90° C. and nitrogen was run through the system for 30 minutes (RPM=300). Once the temperature had stabilized, 35.0 g of finely ground BSPE obtained from Example 1 was added to the flask. The resulting solution was opaque and white with a blue tinge. The BSPE was mixed for 1 hour to disperse it. 0.12 g of $AgNO_3$ was dissolved in 5 mL deionized water and added to the solution dropwise (1 drop/second). A color change to brown was observed. After the completion of $AgNO_3$ addition, the set point was reduced to 75° C. Once the temperature had stabilized, 0.0353 g of glutathione (reducing/stabilizing agent) was added. The solution became dark brown. Subsequently, 3.27 g styrene (8% of total monomer) was added to the dark brown solution (RPM=390), followed by dropwise addition of an ammonium persulfate solution (0.1 g ammonium persulfate dissolved in 5 mL deionized water) which acts as an initiator. A color change to purple was observed. After 5 minutes, 36.73 g of styrene monomer was added dropwise over 40 minutes. The solution was pale purple after the completion of monomer addition. The reaction was run for 4 hours at 75° C. (RPM=390). The resulting solution was then allowed to cool to room temperature. The final appearance was a grey, opaque solution.

Example 7

This Example shows the formation of a styrene shell about a BSPE/AgNP core particle prepared in the presence of the reducing agent.

The reaction was carried out in a 3 necked, 500 mL round bottom flask equipped with an overhead stirrer, reflux condenser, thermocouple, hot plate, and nitrogen entrance (the condenser acted as the nitrogen exit). 248 mL of DIW was charged into the flask at room temperature (22° C.). The heat was turned on set to 90° C. and nitrogen was run through the system (RPM=300). Once the temperature had stabilized, 21.61 g of solid BSPE-1 was added to the system in a finely ground state (RPM=300). The solution became hazy and had a pale blue tinge. After 0.5 hrs., 0.1184 g $AgNO_3$ dissolved in 2 mL DIW was added dropwise to the solution at a rate of approx. 1 drop/second (RPM=300). The solution became green/brown. After 0.5 hrs, 5 mL of 1% (w/w %) trisodium citrate solution (reducing agent) was added to the system dropwise at a rate of 1 drop/second. Upon complete addition, the solution was stirred at 90° C. for 2 hours (RPM=300). The solution was allowed to cool to room temperature (RPM=300). The final appearance was a brown, opaque solution.

Table 1 shows particle characterization for coated and uncoated core particles comprising sulfonated polyester silver nanoparticles with or without silver nanoparticles. The particle size and zeta potential of all samples are comparable except for a couple of outliers (e.g., Example 5's zeta potential and Example 6's particle size). Example 5 has a higher zeta potential compared to the other samples due to the contribution of the carboxyl groups from oleic acid which slightly increases the negative surface charge of the nanoparticles. Example 6 contains a higher loading of styrene and glutathione which both contribute to the higher particle size compared to the other samples.

TABLE 1

| Example | Reducing Agent | % Styrene relative to BSPE | Theoretical % Solids | Loading [$AgNO_3$] (M) | Loading [$AgNO_3$] (w/w %) | Actual % Solids | Particle Size D50 (nm) | Zeta Potential (mV) |
|---|---|---|---|---|---|---|---|---|
| 2 | none | 0 | 28.57% | 0 | 0.00% | 29.46% | 31.8 | −58.9 |
| 3 | none | 44 | 26.49% | 0 | 0.00% | 26.54% | 30.1 | −60.1 |
| 4 | none | 44 | 26.51% | 2.08E−03 | 0.04% | 26.57% | 31.3 | −61.8 |
| 5 | oleic acid | 44 | 26.65% | 4.87E−03 | 0.07% | 22.88% | 34.3 | −65.9 |
| 6 | glutathione | 53 | 23.14% | 2.44E−03 | 0.04% | 22.00% | 47.3 | −59.0 |
| 7 | Trisodium citrate | 0 | 8.00% | 2.73E−03 | 0.05% | 7.58% | 25.4 | −55.8 |

Example 8

This Example shows the preparation of a styrenated BSPE/AgNP powder (i.e., styrenic shell/BSPE/AgNP powder)

In a 2 L glass reactor, a latex emulsion containing 200 g of styrenic/BSPE-AgNP composite obtained from Example 5 and 200 g of deionized water is premixed to give total solids of 13.3%, the pH is adjusted from about 5.0 to 3.0 with 0.3 M nitric acid. The slurry is then homogenized using an IKA ULTRA TURRAX T50 homogenizer operating at about 3,000-4,000 RPM. During homogenization, about 28 g of a flocculent mixture containing about 2.8 g polyaluminum chloride mixture and about 25.2 g 0.02 M nitric acid solution is added to the slurry. Thereafter, the 2 L glass reactor is transferred to a heating mantle; the RPM is set to 230 and heated to a temperature of about 50° C. where samples are taken to determine the average toner particle size. Once the particle size of the slurry of about 15 microns as measured with a Coulter Counter is achieved, freezing begins with the pH of the slurry being adjusted to about 4.5-5.0 using a 4% NaOH solution while also decreasing the reactor RPM to 75. The reactor temperature is ramped to 96° C. Once at the coalescence temperature, the slurry is coalesced for about 3 hours until the particle circularity is between 0.975-0.980 as measured by the Flow Particle Image Analysis (FPIA) instrument. The slurry is then cooled. The final particle size of the slurry is about 15.5 microns, GSDv 1.25, GSDn 1.25 and a circularity of 0.981. The slurry is then discharged from the reactor and the particles are filtered from the mother liquor and washed 2 times with deionized water (DIW). The final slurry is re-dispersed into 200 mL of deionized water, frozen via shell-freezer, and placed on drier for 3 days to result in dry particles to be used for SLS additive manufacturing.

Example 9

This Example tests the robustness of the hybrid composites (i.e., styrenic shell/BSPE/AgNPs) obtained from Examples 3-7 (A) Solvent Resistance The solvent resistance test tests the ability of a composite to resist chemicals or solvents that would otherwise degrade the polymer.

A pellet was made by compressing approximately 0.50 g of sample under 5 tons of pressure for 5 minutes using a hand press. The initial weight of the pellet was measured. 10 mL of solvent was added to the vials. After 24 hours, the solutions were inverted 5 times. After 48 hours, the pellet was placed on a weighing dish. The pellet was allowed to air dry. The final mass of the pellet was measured and recorded once it achieved constant weight (+/−0.0001 g).

BSPE alone cannot withstand treatment with solvents with a high dielectric constant/high polarity (i.e., methanol) very well. Although it was not completely dissolved after 48 hours, the physical properties changed dramatically to a stringy gelatinous blob.

Figure 2A:
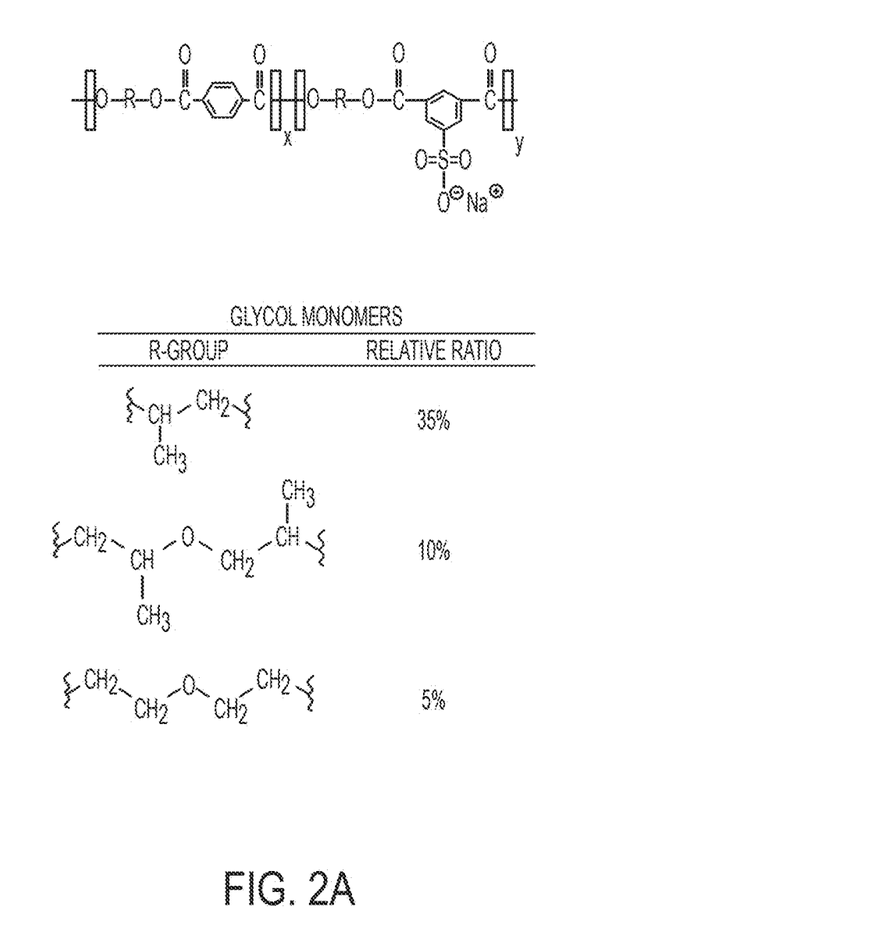
FIGS. 2A and 2B show a schematic of a possible mechanism of the preparation of dry particles.
Figure 2B:
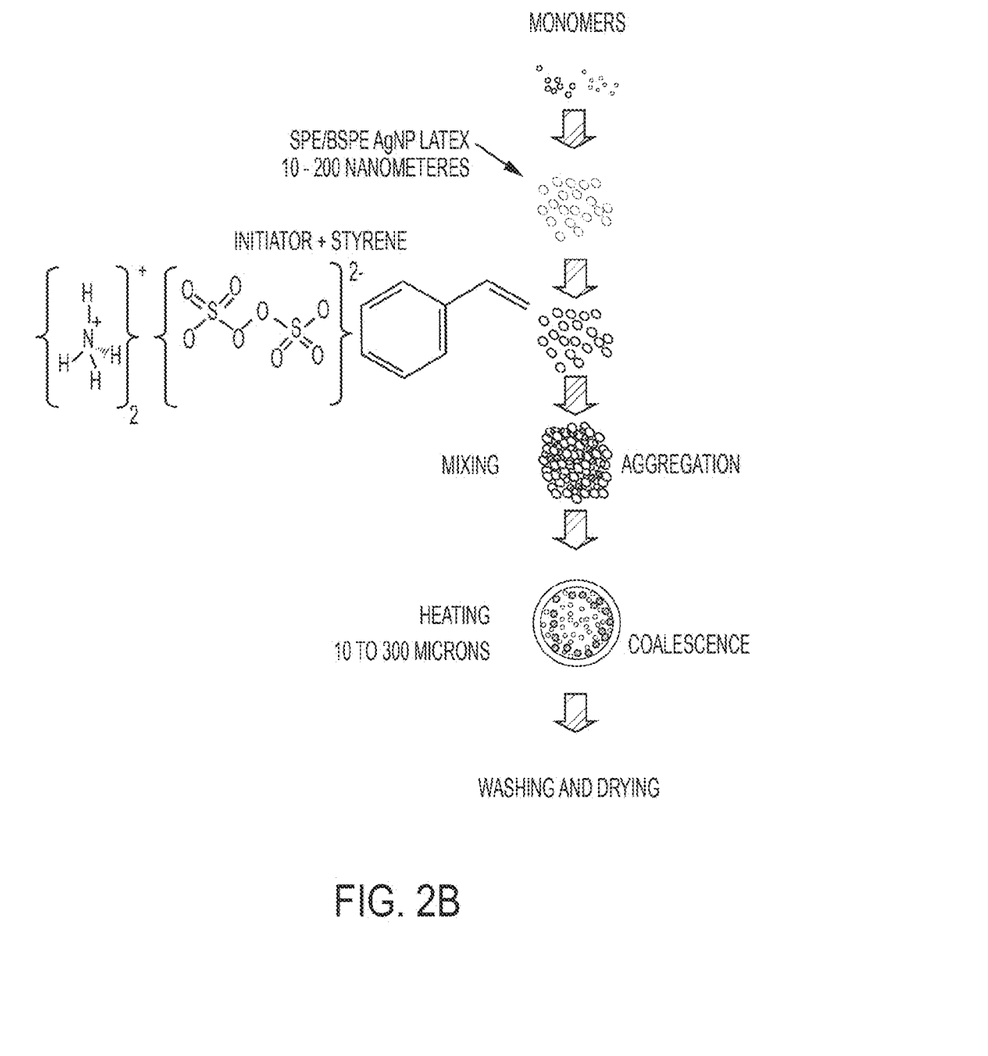

A pellet of pure poly(styrene) sample kept its form as a pellet and was almost completely undissolved. Example 4 had good resistance to methanol compared to other hybrid nanocomposites; this sample had well dispersed AgNPs within the organic matrix as seen in FIG. 2.

Overall, the styrenation of sulfonated polyester AgNPs improved its resistance to methanol. All the BSPE/Styrene AgNPs hybrids remained as distinct pellets in methanol with 85-90% of the pellet undissolved after 48 hrs. When less polar (low dielectric constant) solvents were used for the resistance test most of the samples dissolved.

Table 2 shows results of the solvent resistance results for BSPE/Styrenated AgNPs compared to 100% BSPE or polystyrene.

| Vial | Example | Solvent | % Dissolved | Initial Appearance of Pellet | Final Appearance of Pellet |
|---|---|---|---|---|---|
| 1 | 3 | THF | 100.0% | white | completely dissolved |
| 2 |   | MEK | 100.0% | white | completely dissolved |
| 3 |   | methanol | 10.0% | white | White |
| 4 | 5 | THF | 100.0% | brown | completely dissolved |
| 5 |   | MEK | 100.0% | brown | completely dissolved |
| 6 |   | methanol | 11.5% | brown | brown, some cracking on the sides |
| 7 | 4 | THF | 100.0% | off white | completely dissolved |
| 8 |   | MEK | 100.0% | off white | completely dissolved |
| 9 |   | methanol | 7.0% | off white | white, some cracking on sides |
| 10 | 6 | THF | 100.0% | beige | completely dissolved |
| 11 |   | MEK | 100.0% | beige | completely dissolved |
| 12 |   | methanol | 12.0% | beige | Beige |
| 13 | 2 (BSPE only) | THF | 100.0% | white | completely dissolved |
| 14 |   | MEK | 100.0% | white | completely dissolved |
| 15 |   | methanol | gelled | white | sticky/stringy white polymer, not a pellet |
| 16 | Polystyrene; Sigma Aldrich Mw = 13K | THF | 100.0% | white | completely dissolved |
| 17 |   | MEK | 100.0% | white | completely dissolved |
| 18 |   | methanol | 1.0% | white | white pellet |

(B) Thermal Degradation Resistance

As shown in Table 3, the polymer shell-protected (e.g., styrenic/BSPE/AgNPs obtained from Example 6) shows only about 50% degradation at 400° C. by thermogravimetric analysis (TGA), while uncoated BSPE-AgNP composites BSPE alone are 80% decomposed by 400° C. The thermal stability of the styrene-coated BSPE/AgNPs appears to be more complex than that of polystyrene alone. The first major mass loss of the hybrid composite starts around 300° C. (30.86%) but becomes more stable and degrades much slower than uncoated samples and polystyrene control.

TABLE 3

| % weight loss based on on TGA data (RT to 700° C. heating of 100% of sample) | Styrenic/ BSPE/ AgNPs (Example 6) | BSPE-Ag (Example 7) | Control BSPE (Example 2) | Control Polystyrene |
|---|---|---|---|---|
| Weight (%) loss from start to 300° C. | 30.86% | 10.04% | 17.26% | 0.92% |
| Weight (%) loss from 300 to 400° C. | 46.49% | 79.63% | 82.05% | 98.85%* |
| Weight (%) loss from 400 to 500° C. | 93.38% | 89.53% | 89.30% | |
| Weight (%) loss from 500 to 700° C. | 98.41% | 97.15% | 97.76% | 0.00% |
| Residual (%) | 1.60% | 2.84% | 2.21% | 0.15% |
| Total | 100.01% | 99.99% | 99.96% | 99.92% |

*Polystyrene degrades as one single peak starting at around 300° C.

(C) Acid/base Resistance

The acid/base resistance test tests the ability of a composite acids and bases that would otherwise degrade the composite.

A pellet was made by compressing approximately 0.50 g of sample under 5 tons of pressure for 5 minutes using a hand press. The initial weight of the pellet was measured. 10 mL of acid/base (10% Nitric acid, 10% NaOH or 30% Sulfuric acid) was added to the vials. After 96 hours, the pellet was placed on a weighing dish. The pellet was allowed to air dry for 3 days. The final mass of the pellet was measured and recorded. This procedure was adapted from an article published in Industrial and Engineering Chemistry. Church, J. M et al. Ind. Eng. Chem., 47 (12):2456-2462 (1955).

Table 4 shows Acid/Base Resistance results for BSPE/Styrenated AgNPs compared to 100% BSPE or polystyrene. The value for the % dissolved for sample from Example 3 was corrected to account for 5% sample loss during measurement.

The results of the soak test show that composites are largely susceptible to base catalyzed degradation. The sample of BSPE alone showed the highest amount of it's initial mass dissolved in 10% NaOH. In comparison, styrene alone did not dissolve. The BSPE-Styrene (Example 3) and BSPE-Styrene-Silver samples (Examples 5 and 6) were less susceptible to degradation in an alkaline environment than the sample that was not styrenated. Samples did not dissolve appreciably in acidic environments. The higher amount of dissolved material in acid for Example 6 is likely the result of the hydrolysis of glutathione in acid. Olson, C. K. et al. J. Biol. Chem., 186:731-735 (1950).

In sum, the addition of a styrene shell to the BSPE/AgNPs results in an improvement under basic conditions by 20 to 30%. No significant improvement is observed in acidic environments. In some cases, BSPE with embedded AgNPs may still become susceptible to alkali environments when the ester linkages are split to an acid and alcohol by hydrolysis. Additionally the hydrolysis may be acid or base catalyzed (e.g., polymer coated materials exposed to basic or acidic cleaning products or acid rain). Polymerizing a shell of polystyrene, around the BSPE/AgNP core provides substantially improved rigidity and strength of the organic/inorganic hybrid composite core materials.

TABLE 4

| Vial | Example | Acid/Base | % Dissolved | % change relative to BSPE (Example 2) |
|---|---|---|---|---|
| 1 | 3 | 10% Nitric Acid | 0.0% | |
| 2 | | 10% NaOH | 32.2% | 30.9% |
| 3 | | 30% Sulfuric Acid | 0.0% | |
| 4 | 5 | 10% Nitric Acid | 4.3% | |
| 5 | | 10% NaOH | 45.8% | 17.2% |
| 6 | | 30% Sulfuric Acid | 4.1% | |
| 7 | 6 | 10% Nitric Acid | 5.4% | |
| 8 | | 10% NaOH | 35.6% | 27.4% |
| 9 | | 30% Sulfuric Acid | 14.5% | |
| 10 | 2 | 10% Nitric Acid | 2.0% | |
| 11 | (BSPE only) | 10% NaOH | 63.0% | 0% |
| 12 | | 30% Sulfuric Acid | 0.00% | |
| 13 | Polystyrene; Sigma Aldrich Mw = 13K | 10% Nitric Acid | 0.0% | |
| 14 | | 10% NaOH | 0.0% | |
| 15 | | 30% Sulfuric Acid | 0.0% | |

Example 9

This Example shows wet deposition of BSPE-AgNPs antibacterial particles to mimic glass microfiber membrane fusing A suspension of the particles prepared in Example 3 was prepared in water containing a small amount of Triton-X 100 surfactant. An amount of this suspension corresponding to 9.62 mg of particles was passed through a glass microfiber membrane through a cup with an exposed surface area of 9.62 cm$^2$. The retained particles and filter paper were dried at room temperature, then enveloped in Mylar film and passed through a GBC laminator set to 120° C.

Results after 3 days of incubation at 37° C. confirmed that the fused BSPE-AgNP particles showed no bacteria growth around the particle swatch or on the swatch itself. This zone of inhibition or "halo-effect" is quite large which means that the silver ions are easily released from the particles over a short period of time.

Example 10

This Example shows a SLS sintering process of the BSPE-AgNPs powder

Approximately 10 g of particles obtained from Example 7 are spread into a 4" petri dish and subject to laser annealing for 10 seconds. (Epilog Zing Laser Cutter, 40 W laser). Particles are then welded together to form solid monoliths.

What is claimed is:

1. A composite powder for use in selective laser sintering, comprising:
    a core particle comprising:
        a sulfonated polyester matrix; and
        a plurality of silver nanoparticles dispersed within the matrix;
    and
        a shell polymer disposed about the core particle;
    wherein the silver nanoparticle is present in the composite powder in a range from about 0.5 ppm to about 50,000 ppm; and further wherein the composite powder has a particle size of from about 10 microns to about 300 microns.

2. The composite powder of claim 1, wherein the sulfonated polyester has a glass transition (Tg) temperature of from about 45° C. to about 95° C.

3. The composite powder of claim 1, wherein the sulfonated polyester matrix comprises a branched polymer.

4. The composite powder of claim 1, wherein the sulfonated polyester matrix comprises a linear polymer.

5. The composite powder of claim 1, wherein the powder composite has a spherical structure.

6. The composite powder of claim 1, wherein the sulfonated polyester matrix comprises lithium, potassium, or sodium salt of a polymer selected from the group consisting of poly(1,2-propylene-5-sulfoisophthalate), poly(neopentylene-5-sulfoisophthalate), poly(diethylene-5-sulfoisophthalate), copoly-(1,2-propylene-5-sulfoisophthalate)-copoly-(1,2-propylene-terphthalate), copoly-(1,2-propylenediethylene-5-sulfoisophthalate)-copoly-(1,2-propylene-diethylene-terephthalatephthalate), copoly (ethylene-neopentylene-5-sulfoisophthalate)-copoly-(ethylene-neopentylene-terephthalatephthalate), and copoly (propoxylated bisphenol A)-copoly-(propoxylated bisphenol A-5-sulfoisophthalate).

7. The composite of claim 1, wherein the sulfonated polyester matrix comprises a polyol monomer unit selected from the group consisting of trimethylolpropane, 1,2-propanediol, diethylene glycol, and combinations thereof.

8. The composite of claim 1, wherein the sulfonated polyester matrix comprises a diacid monomer unit selected from the group consisting of terephthalic acid, sulfonated isophthalic acid, and combinations thereof.

9. The composite of claim 1, wherein the shell polymer comprises a styrene monomer.

10. The composite of claim 1, wherein the shell polymer further comprises at least one vinyl monomer selected from the group consisting of methyl acrylate, ethyl acrylate, butyl acrylate, isobutyl acrylate, dodecyl acrylate, n-octyl acrylate, 2-ethylhexyl acrylate, 2-chloroethyl acrylate, phenyl acrylate, β-carboxyethyl acrylate, methyl α-chloro acrylate, methyl methacrylate, ethyl methacrylate, butyl methacrylate, butadiene, isoprene, methacrylonitrile, acrylonitrile, methyl vinyl ether, vinyl isobutyl ether, vinyl ethyl ether, vinyl acetate, vinyl propionate, vinyl benzoate, vinyl butyrate, vinyl methyl ketone, vinyl hexyl ketone, and methyl isopropenyl ketone, vinylidene chloride, vinylidene chloro fluoride, N-vinylindole, N-vinyl pyrrolidene, acrylic acid, methacrylic acid, acrylamide, methacrylamide, vinyl pyridine, vinyl pyrrolidone, vinyl N-methylpyridinium chloride, vinyl naphthalene, p-chlorostyrene, vinyl chloride, vinyl fluoride, ethylene, propylene, butylene, and isobutylene.

11. A three-dimensional article comprising:
    a composite powder comprising:
        a core particle comprising:
        a sulfonated polyester matrix; and
        a plurality of silver nanoparticles dispersed within the matrix;
    and
        a shell polymer disposed about the core particle;
    wherein the silver nanoparticle is present in the composite powder in a range from about 0.5 ppm to about 50,000 ppm; and further wherein the composite powder has a particle size of from about 10 microns to about 300 microns.

12. The three-dimensional article of claim 11, wherein the article is selected from the group consisting of a biochemical sensor, an optical detector, an antibacterial, a textile, a cosmetic, an electronic component, a fiber, and a cryogenic superconducting material.

* * * * *